United States Patent [19]

Sie et al.

[11] Patent Number: 4,935,398

[45] Date of Patent: Jun. 19, 1990

[54] PROCESS FOR THE PRODUCTION OF METHANOL AND A COMPOSITION SUITABLE FOR USE AS A CATALYST IN SAID PROCESS

[75] Inventors: Swan T. Sie; Eit Drent; Willem W. Jager, all of Amsterdam, Netherlands

[73] Assignee: Shell Oil Company, Houston, Tex.

[21] Appl. No.: 358,967

[22] Filed: May 30, 1989

Related U.S. Application Data

[62] Division of Ser. No. 185,622, Apr. 25, 1988, Pat. No. 4,873,267.

[30] Foreign Application Priority Data

Apr. 29, 1987 [GB] United Kingdom ............... 871072

[51] Int. Cl.$^5$ ............................................. B01J 31/04
[52] U.S. Cl. ............................................. 502/117
[58] Field of Search ............................................. 502/117

[56] References Cited

U.S. PATENT DOCUMENTS

| | | | |
|---|---|---|---|
| 3,676,523 | 7/1972 | Mason | 260/688.15 |
| 4,271,323 | 6/1981 | Durano et al. | 502/117 X |
| 4,357,478 | 11/1982 | Hillion et al. | 568/816 |
| 4,619,946 | 10/1986 | Sapienza et al. | 518/700 |
| 4,716,138 | 12/1987 | Murray | 502/117 |

FOREIGN PATENT DOCUMENTS

| | | |
|---|---|---|
| 56-169634 | 12/1981 | Japan . |
| 1002721 | 8/1965 | United Kingdom . |
| 2058074 | 8/1979 | United Kingdom . |
| 1562780 | 3/1980 | United Kingdom . |

*Primary Examiner*—Patrick P. Garvin
*Attorney, Agent, or Firm*—Y. Grace Tsang

[57] ABSTRACT

A process for the preparation of methanol by contacting CO and $H_2$ with a novel catalytic system formed by combining (a) a nickel salt of a carboxylic acid having a $pK_a > 4.76$, (b) an alcohol, and (c) a hydride of an alkaki metal or of an alkaline earth metal.

9 Claims, No Drawings

PROCESS FOR THE PRODUCTION OF METHANOL AND A COMPOSITION SUITABLE FOR USE AS A CATALYST IN SAID PROCESS

This is a division of application Ser. No. 185,622 filed Apr. 25, 1988 and now Pat. No. 4,873,267.

FIELD OF THE INVENTION

The invention relates to a process for the production of methanol. The invention also relates to a novel composition suitable for use as a catalyst in said process.

BACKGROUND OF THE INVENTION

A process for the production of methanol is described in U.S. Pat. No. 4,619,946 issued Oct. 28, 1980. The patent concerns reacting carbon monoxide with hydrogen in the presence of a catalytic system of the type NaH-RONa-nickel acetate in which R represents an alkyl group having 1–6 carbon atoms. This catalytic system can be made more active by "conditioning," involving contacting for a prolonged time with a gaseous mixture comprising carbon monoxide and hydrogen at such an elevated temperature and elevated pressure that a substantial amount of carbon monoxide and hydrogen is consumed for this conditioning.

Another process for the production of methanol is described in Japanese patent application publication No. 56-169,634, published Dec. 26, 1981, which concerns reacting carbon monoxide and hydrogen in the presence of a catalyst comprising a nickel compound and an alkali metal alkoxide.

It is an object of the present invention to produce methanol in the presence of a catalytic system having enhanced activity.

It is another object of the present invention to produce methanol in the presence of a catalytic system that retains its activity for a long time.

SUMMARY OF THE INVENTION

Accordingly, the invention provides a process for the production of methanol which process comprises contacting a gaseous mixture comprising carbon monoxide and hydrogen with a catalytic system prepared by combining the following components:

component (a): a nickel salt of a carboxylic acid having a $pK_a$, measured in aqueous solution at 25° C., of more than 4.76;
component (b): - an alcohol; and
component (c): a hydride of an alkali metal and/or a hydride of an alkaline earth metal.

The anion of the salt in component (a) may be derived from a great variety of carboxylic acids having a $pK_a$, measured in aqueous solution at 25° C., of more than 4.76. Preference is given to alkanoic acids, particularly to those having in the range of from 3 to 10 carbon atoms per molecule. Propanoic acid is most preferred.

Other examples of suitable carboxylic acids of which anions are present in component (a) are butanoic acid ($PK_a=4.81$), 2-methylpropanoic acid ($pK_a=4.84$), pentanoic acid ($pK_a=4.82$), 3-methylbutanoic acid ($pK_a=4.77$), 2,2-dimethylpropanoic acid ($pK_a=5.02$), hexanoic acid ($pK_a=4.88$), heptanoic acid ($pK_a=4.89$) and octanoic acid ($pK_a=4.89$). Component (a) is not derived from acetic acid as the only acid. Acetic acid has a $pK_a$ of 4.75. It is, however, not excluded from the scope of the invention that component (a) contains a mixture of anion(s) of carboxylic acid(s) having $pK_a$ of more than 4.76 and anion(s) of acetic acid and/or formic acid.

A mixture of the above-mentioned salts as well as other suitable salts may be used in component (a). For example, a mixture of a propionate and a butyrate or a mixture of a 2,2-dimethylpropionate and a propionate can be used. It is also possible to use as component (a) a mixture of (i) a salt containing a cation of an element of Group VIII and an anion of an acid having a $pK_a$ of more than 4.76, and (ii) a salt containing a cation of an element of Group VIII and an anion of an acid having a $pK_a$ of less than 4.70. The use of the latter salts is described in British patent application No. 8708004, filed Apr. 3, 1987.

The salts in component (a) may contain crystal water, but are preferably free therefrom.

The alcohol of component (b) may be aromatic or cycloaliphatic but is preferably aliphatic. Preference is given to alkanols, in particular to those having in the range of from 1 to 20 carbon atoms per molecule. Among the latter alkanols those having in the range of from 4 to 12 carbon atoms per molecule are preferred, because such alkanols can be easily separated from methanol by means of distillation. Examples of such alkanols are tert-butyl alcohol, tert-pentyl alcohol, hexanol, heptanol and alkanols having in the range of from 8 to 12 carbon atoms per molecule. Tert-butyl alcohol and tert-pentyl alcohol are particularly preferred. Dihydric alcohols may also be used, for example, ethylene glycol, propylene glycol, 1,3-dihydroxypropane, 1,2-butanediol, 1,3-butanediol, 1,4-butanediol, 2,3-butanediol or 1,2-pentanediol. Component (b) may also be glycerol.

Component (b) may be a mixture of alcohols, for example of tert-butyl alcohol and ethylene glycol or of tert-pentyl alcohol and 1,4-butanediol.

Component (c) may be a hydride of lithium, sodium, potassium, rubidium, cesium, calcium, strontium, barium or magnesium. Preference is given to sodium hydride. The hydride may be added as such, but it has been found that the hydride may advantageously be added as a suspension in an inert diluent, for example, a mineral oil, such as a heavy hydrocarbon oil, preferably a so-called white paraffin oil.

If desired, an alcoholate of an alkali metal or an alcoholate of an alkaline earth metal may also be combined in the catalytic system. This alcoholate is preferably a sodium alcoholate or a potassium alcoholate. Among the alcoholates preference is given to alkoxides, particularly to those having in the range of from 1 to 20 carbon atoms per molecule, such as sodium methoxide, sodium ethoxide, sodium propoxide, sodium butoxide, sodium isobutoxide, sodium tert-pentoxide and potassium 2-methyldodec-2-oxide.

It has, furthermore, been found that the activity of the catalytic system can be further enhanced by a pre-treatment. According to a preferred embodiment of the present invention the catalytic system is pre-treated by contacting it for a prolonged time with a gaseous mixture comprising carbon monoxide and hydrogen at such an elevated temperature and elevated pressure that no substantial consumption of carbon monoxide and hydrogen takes place. Usually, a period in the range of from 10 minutes to 5 hours at a temperature between 30° C. and 150° C. and a pressure between 5 and 100 bar is sufficient for the pre-treatment. The pre-treatment ends when the pressure progressively starts decreasing, which is a signal for formation of substantial amounts of methanol. Surprisingly, the present pre-treatment consumes very little carbon monoxide and hydrogen but yet results in the formation of a catalytic system having a considerably enhanced activity for the production of methanol. At the end of the pre-treatment, the temperature may be adjusted to the required reaction temperature, which is a value at which substantial amounts of methanol are produced. This adjustment may be an increase of the temperature, but it is also possible that the temperature can be decreased. Such an increase or decrease of the temperature will usually be over a range of 10° C. to 50° C. It is possible, however, that no adjustment of the temperature is required at all, pre-treatment and methanol production being carried out at substantially the same temperature.

The process according to the present invention may be carried out at a temperature and a pressure which are not critical and may vary within wide ranges. Preferably, a temperature in the range of 30° C. to 150° C. and a pressure in the range of from 5 to 100 bars are used.

The process according to the present invention may be carried out with an organic diluent in which the catalytic system is present, at least partly, as a suspension. Suitably, a weight ratio of organic diluent to component (a) in the range of from 0.1 to 5000 is used, but this weight ratio may be lower than 0.1 or higher than 5000. The process according to the present invention is preferably carried out using a molar ratio of component (c) to component (a) in the range of from 0.5:1 to 100:1 and, more preferably, from 1:1 to 50:1, but the use of molar ratios below 0.5 and above 100 is not excluded from the scope of this invention. The process may be carried out using a molar ratio of component (b) to component (a), which is not critical and may vary within wide ranges, preferably in the range of from 0.1 to 1 to 100 to 1.

Any inert diluent may in principle be used. Examples of suitable diluents are ketones such as acetone, methyl ethyl ketone, methyl isobutyl ketone, acetophenone, cyclohexanone and acetylacetone; ethers such as anisole, 2,5,8-trioxanonane (also referred to as "diglyme"), diethyl ether, diphenyl ether, diisopropyl ether and tetrahydrofuran; aromatic hydrocarbons such as benzene, toluene, the three xylenes and ethylbenzene; halogenated aromatic compounds such as chlorobenzene and o-dichlorobenzene., halogenated alkanes such as dichloromethane and carbon tetrachloride., alkanes such as hexane, heptane, octane, 2,2,3-trimethylpentane and kerosene fractions; cycloalkanes such as cyclohexane and methylcyclohexane; nitriles such as benzonitrile and acetonitrile; sulfoxides such as dimethyl sulfoxide; sulfones such as diisopropyl sulfone, tetrahydrothiophene-1,1-dioxide (also referred to as "sulfolane"), 2-methyl-4-butylsulfolane and 3-methylsulfolane. Mixtures of two or more solvents may be used. Very good results have been obtained with ethers.

The carbon monoxide and hydrogen may be used as pure gases or diluted with an inert gas such as noble gas or nitrogen. The process according to the present invention may be carried out using a molar ratio carbon monoxide to hydrogen in the gaseous mixture, which is not critical and may vary within wide ranges, suitable in the range of from 1:0.2 to 1:20. The carbon monoxide and hydrogen may be obtained by partial oxidation of hydrocarbons, for example, of natural gas. The methanol produced according to the invention may be used for a variety of purposes, for example, for the manufacture of synthetic gasoline, as a fuel component and for the production of methyl tert-butyl ether.

The process according to the present invention may be carried out batchwise, semi-continuously or continuously.

The invention also provides a novel composition prepared by combining the following components:
component (a): a nickel salt of a carboxylic acid having a $pK_a$, measured in aqueous solution at 25° C., of more than 4.76.,
component (b): an alcohol; and
component (c): a hydride of an alkali metal and/or a hydride of an alkaline earth metal.

Said novel composition may be used as a catalytic system in the process according to the present invention.

The ranges, limitations and steps provided in the instant specification and claims are those which are believed to particularly point out and distinctly claim the instant invention. It is, however, understood that other ranges, limitations and steps that perform substantially the same function in substantially the same manner to obtain the same or substantially the same result are intended to be within the scope of the instant invention as defined by the instant specification and claims.

The invention is further illustrated by means of the following Examples. Each experiment was carried out in a 300 ml HASTELLOY® C autoclave provided with a magnetic stirrer. The sodium hydride was used as a suspension in white paraffin oil containing 80% by weight of NaH. The reaction mixtures were analysed by means of gas-liquid chromatography.

EXAMPLE 1

The autoclave was charged under a nitrogen atmosphere with diglyme (50 ml), anhydrous nickel propionate (10 mmol), sodium hydride (60 mmol) and tert-pentyl alcohol (20 mmol), heated to a temperature of 45° C. with stirring and kept at this temperature for 0.5 hours. Then, a solution of tert-pentyl alcohol (30 mmol) in diglyme (50 ml) was introduced into the autoclave, the autoclave was sealed and a mixture of 1 volume of carbon monoxide and 2 volumes of hydrogen was admitted until a pressure of 45 bar was obtained.

The autoclave was further heated to a temperature of 80° C. and kept at this temperature for 2 hours. Then, the autoclave was further heated to a temperature of 100° C. and kept at this temperature for 2 hour. During this period of 2 hours the autoclave was four times repressurized by increasing the partial pressures of hydrogen and carbon monoxide with 24 bar and 8 bar, respectively, the first time after 25 minutes, the second time after 45 minutes, the third time after 1 hour and 10 minutes and the fourth time after 1 hour and 40 minutes.

At the end of this period of 2 hours the pressure in the autoclave was still decreasing which indicates that the catalytic system was till active. At this moment the autoclave was allowed to adopt ambient temperature and then opened.

The reaction mixture contained a yellow solid substance and 11.3 g of methanol.

COMPARATIVE EXPERIMENT A

This experiment is identical with that of Example 1 until the moment the autoclave had reached a temperature of 100° C., with the exception of replacing the nickel propionate (10 mmol) with anhydrous nickel acetate (10 mmol).

The autoclave was kept at a temperature of 100° C. for 2 hours. During this period of 2 hours the autoclave was twice repressurized by increasing the partial pressures of hydrogen and carbon monoxide with 24 bar and 8 bar, respectively, the first time after 5 minutes and the second time after 35 minutes.

The pressure in the autoclave ceased decreasing after the second addition of carbon monoxide and hydrogen which indicates that the catalytic system had lost its activity. The autoclave was allowed to adopt ambient temperature at the end of the period of 2 hours and then opened.

The reaction mixture contained 7.5 g methanol. Comparison with Example 1 shows that the presence of nickel proprionate renders the catalytic system more active than the presence of nickel acetate.

COMPARATIVE EXPERIMENT B

The autoclave was charged under a nitrogen atmosphere with diglyme (50 ml), nickel acetylacetonate (10 mmol), sodium hydride (60 mmol) and tert-butyl alcohol (20 mmol), heated to a temperature of 45° C. with stirring and kept at this temperature for 2 hours. Then, a solution of tertbutyl alcohol (30 mmol) in diglyme (50 ml) was introduced into the autoclave, the autoclave was sealed and a mixture of 1 volume of carbon monoxide and 2 volumes of hydrogen was admitted until a pressure of 45 bar was obtained.

The autoclave was further heated to a temperature of 100° C. and kept at this temperature for 2 hours. The pressure remained constant during this period which indicates that the catalyst had lost its activity. At this moment the autoclave was allowed to adopt ambient temperature and then depressurized. The reaction mixture contained a black-green solid substance and no methanol.

COMPARATIVE EXPERIMENT C

Comparative Experiment B was repeated with the difference that nickel acetylacetonate (10 mmol) was replaced with nickel cyanide (10 mmol). The result was the same as in Comparative Experiment B.

EXAMPLE 2

The autoclave was charged under a nitrogen atmosphere with diglyme (50 ml), anhydrous nickel propionate (10 mmol), sodium hydride (60 mmol) and tert-pentyl alcohol (20 mmol), heated to a temperature of 45° C. with stirring and kept at this temperature for 0.5 hour. Then, a solution of tert-pentyl alcohol (20 ml) in diglyme (50 ml) was introduced into the autoclave, the autoclave was pressurized with 15 bar of carbon monoxide and 30 bar of hydrogen, further heated to a temperature of 80° C. and kept at this temperature for 4 hours. During this period of 4 hours the autoclave was five times repressurized by increasing the partial pressures of hydrogen and carbon monoxide with 24 bar and 8 bar, respectively, the first time after 20 minutes, the second time after 55 minutes, the third time after 1 hour 30 minutes, the fourth time after 2 hours and the fifth time after 3 hours.

At the end of the period of 4 hours the pressure in the autoclave was still decreasing which indicates that the catalytic system was still active. At this moment the autoclave was allowed to adopt ambient temperature and then opened. The reaction mixture contained 16 g of methanol.

Comparison with Example 1 shows that the second addition of tert-pentyl alcohol has enhanced the yield of methanol.

EXAMPLE 3

Example 1 was repeated with the difference that nickel propionate (10 mmol) was replaced with nickel pivalate (10 mmol) and that the following procedure was followed when a pressure of 45 bar was obtained. The autoclave was further heated to a temperature of 80° C. and kept at this temperature for 2 hours. During this period of 2 hours the autoclave was once repressurized by increasing the partial pressure of hydrogen and carbon monoxide with 24 bar and 8 bar, respectively, after 1 hour 30 minutes.

At the end of this period of 2 hours the pressure in the autoclave was still decreasing which indicates that the catalytic system was still active. At this moment the autoclave was allowed to adopt ambient temperature and then opened. The reaction mixture contained 2 g of methanol.

EXAMPLE 4

The autoclave was charged under a nitrogen atmosphere with diglyme (50 ml), anhydrous nickel pivalate (10 mmol), sodium hydride (60 mmol) and tert-pentyl alcohol (20 mmol), heated to a temperature of 45° C. with stirring and kept as this temperature for 0.5 hour. Then, a solution of tert-pentyl alcohol (20 ml) in diglyme (50 ml) was introduced into the autoclave, the autoclave was sealed and a mixture of 1 volume of carbon monoxide and 2 volumes of hydrogen was admitted until a pressure of 45 bar was obtained.

The autoclave was further heated to a temperature of 60° C. and kept at this temperature for 5 hours. During this period of 5 hours the autoclave was three times repressurized by increasing the partial pressures of hydrogen and carbon monoxide with 24 bar and 8 bar, respectively, the first time after 1 hour, the second time after 2 hours, and the third time after 3 hours.

At the end of this period of 5 hours the pressure in the autoclave was still decreasing which indicates that the catalytic system was still active. At this moment the autoclave was allowed to adopt ambient temperature and then opened.

The reaction mixture contained.7.5 g of methanol.

Comparison with Example 3 shows that the second addition of tert-pentyl alcohol has enhanced the yield of methanol.

What is claimed is:

1. A catalytic composition prepared by combining the following components:
   component (a): a nickel salt of a carboxylic acid having a $pK_a$, measured in aqueous solution at 25° C., of more than 4.76;
   component (b): an alcohol; and
   component (c): hydride selected from the group consisting of a hydride of an alkali metal, a hydride of an alkaline earth metal, and a mixture thereof.

2. The composition as claimed in claim 1, in which the salt in component (a) is nickel propionate.

3. The composition as claimed in claim 1, in which the alcohol in component (b) is an alkanol.

4. The composition as claimed in claim 3, in which the alkanol has in the range of from 4 to 12 carbon atoms per molecule.

5. The composition as claimed in claim 4, in which the alkanol is tert-butyl alcohol or tert-pentyl alcohol.

6. The composition as claimed in claims 1, in which the hydride in component (c) is sodium hydride.

7. The composition as claimed in claim 1, which further comprises an alcoholate of an alkali metal or an alcoholate of an alkaline earth metal.

8. A catalytic composition prepared by combining:
(a) nickel propionate,
(b) an alcohol, and
(c) sodium hydride;
wherein said catalytic system is pretreated by contacting with a gaseous mixture comprising carbon monoxide and hydrogen for a period of time ranging from about 10 minutes to about 5 hours at an elevated temperature and an elevated pressure at which no substantial consumption of carbon monoxide and hydrogen takes place; wherein an additional amount of said alcohol is added to the catalytic system at the end of the pre-treatment process.

9. The composition as claimed in claim 8, wherein the composition further comprises an alcoholate of an alkali metal or an alcoholate of an alkaline earth metal, wherein said sodium hydride is suspended in a mineral oil.

* * * * *